US010959875B2

(12) United States Patent
Yousefian

(10) Patent No.: US 10,959,875 B2
(45) Date of Patent: Mar. 30, 2021

(54) MASTICATORY AND AIRWAY STABILIZING ORTHOTIC, AND ASSOCIATED SYSTEMS AND METHODS

(71) Applicant: Joseph Yousefian, Bellevue, WA (US)

(72) Inventor: Joseph Yousefian, Bellevue, WA (US)

( * ) Notice: Subject to any disclaimer, the term of this patent is extended or adjusted under 35 U.S.C. 154(b) by 472 days.

(21) Appl. No.: 15/250,045

(22) Filed: Aug. 29, 2016

(65) Prior Publication Data

US 2017/0056236 A1 Mar. 2, 2017

Related U.S. Application Data

(60) Provisional application No. 62/210,877, filed on Aug. 27, 2015.

(51) Int. Cl.
*A61F 5/56* (2006.01)
*A61C 7/08* (2006.01)
*A61C 7/36* (2006.01)
*A61C 7/10* (2006.01)

(52) U.S. Cl.
CPC .............. *A61F 5/566* (2013.01); *A61C 7/08* (2013.01); *A61C 7/10* (2013.01); *A61C 7/36* (2013.01)

(58) Field of Classification Search
CPC ...... A61F 5/566; A61F 2005/563; A61F 5/56; A61C 7/08; A61C 7/10; A61C 7/36; A61M 16/0488; A61N 1/3611; A61B 5/4818
USPC ........ 128/848, 861; 433/6, 7, 24, 69; 607/42
See application file for complete search history.

(56) References Cited

U.S. PATENT DOCUMENTS

| | | | |
|---|---|---|---|
| 4,433,956 A * | 2/1984 | Witzig | A61C 7/10 433/7 |
| 5,683,244 A | 11/1997 | Truax | |
| 7,712,468 B2 | 5/2010 | Hargadon | |
| 8,833,374 B2 * | 9/2014 | Fallon | A61F 5/566 128/848 |
| 2008/0060659 A1 | 3/2008 | Bonato et al. | |
| 2010/0261133 A1 * | 10/2010 | Lax | A61C 9/0006 433/71 |
| 2014/0135868 A1 * | 5/2014 | Bashyam | A61N 1/3601 607/42 |
| 2014/0190490 A1 | 7/2014 | Walker et al. | |
| 2014/0326253 A1 | 11/2014 | Baratier et al. | |
| 2015/0075540 A1 * | 3/2015 | Dye | A61F 5/566 128/848 |

\* cited by examiner

*Primary Examiner* — Ophelia A Hawthorne
*Assistant Examiner* — Caitlin A Carreiro
(74) *Attorney, Agent, or Firm* — Timothy E. Siegel Patent Law, PLLC; Timothy E. Siegel

(57) ABSTRACT

Systems and methods for treating sleep-disordered breathing and related masticatory and temporomandibular joint disorders are disclosed herein. In one embodiment, an oral appliance for treating the sleep-disordered breathing and/or the related masticatory and temporomandibular joint disorders includes an upper section configured for attachment to upper teeth and a lower section configured for positioning behind lower teeth. The oral appliance also includes an extender connecting the lower section to the upper section. The extender is configured to advance the lower section into a contact with the lower teeth.

18 Claims, 20 Drawing Sheets

CROSS-SECTION 1B-1B

CROSS-SECTION 1B-1B

CROSS-SECTION 1C-1C

CROSS-SECTION 2B-2B

CROSS-SECTION 2B-2B

CROSS-SECTION 4B-4B

CROSS-SECTION 4B-4B

*CROSS-SECTION 4B-4B*

MASTICATORY AND AIRWAY STABILIZING ORTHOTIC, AND ASSOCIATED SYSTEMS AND METHODS

CROSS-REFERENCE TO RELATED APPLICATION

This application claims the benefit of U.S. Provisional Application No. 62/210,877, filed Aug. 27, 2015, the disclosure of which is incorporated herein by reference in its entirety.

FIELD OF THE INVENTION

The present invention relates generally to oral appliances. More particularly, the present invention relates to oral appliances and associated methods for treating sleep-disordered breathing and masticatory and temporomandibular disorders.

BACKGROUND

Sleep-disordered breathing (SDB), and its severe clinical form, obstructive sleep apnea (OSA), are listed as a major cause of excessive sleepiness. SDB is associated with a seven-fold increase in the incidence of accidents at home, at work, and while driving. It is also linked to poor job performance and academic failure.

Those with the OSA stop breathing in their sleep, often hundreds of times during the night. Usually the OSA occurs when the throat muscles and tongue relax during sleep and partially block the opening of the airway. The condition of narrowing of the airway space and retraction of the soft palate and tongue back to the airway can cause the constriction of the upper airway in the retropalatal (behind the palate), retroglossal (behind the tongue), and hypoglossal (behind and below the tongue) area. As a result, the upper airway of the patient becomes constricted and causes resistance to the air passage during sleep, especially in the deeper stage of sleep when the upper airway muscles relax and cannot provide ideal support of the airway. Sleep apnea also can occur in obese people when an excess amount of tissue narrows the airway.

Severe nocturnal snoring, a symptom of SDB, can be a negative factor in family relationships. Other potential health risk factors associated with the OSA include tooth grinding, temporomandibular disorders, facial deformities, ADHD, gastroesophageal reflux disease, premature aging, depression, hypertension, sexual impotence, Alzheimer disease, metabolic syndrome, diabetes, obesity, and more dangerous illnesses such as cancer, heart disease, and stroke.

The occurrence of moderate to severe sleep-disordered breathing (apnea-hypopnea index, measured as events/hour, ≥15) is estimated to about 10% among 30-49-year-old men; 17% among 50-70-year-old men; 3% among 30-49-year-old women; and 9% among 50-70-year-old women. These estimated rates represent substantial increases over the last two decades, with relative increases of between 14% and 55%, depending on the subgroup.

There are several conventional technologies that treat snoring and sleep apnea. Some examples of conventional technologies are continuous positive air pressure (CPAP) therapy, surgery, lifestyle changes, and oral airway dilators, also called lower jaw advancing devices or oral devices (OD). In many instances, CPAP works reasonably well, but it is uncomfortable, and requires wearing a mask attached to a positive pressure pump. Therefore, the compliance rate tends to be low.

Conventional surgery is painful and invasive, and has a success rate of less than 50%. Lifestyle changes, such as weight loss, exercise, no alcohol consumption, dietary counseling, and food restrictions also have low compliance rates.

The conventional ODs generally have higher patient compliance, and can be comfortable and effective, particularly in cases of mild to moderate OSA. However, the conventional ODs are generally bulky and/or restrict tongue protrusion by their design of the anterior mandibular advancement mechanisms. Furthermore, some conventional ODs cause tooth movement or gagging by tongue depression. Some conventional ODs are prone to breakage.

Additionally, many conventional ODs change patient's bite, resulting in a difficult chewing and/or development of masticatory and temporomandibular disorders. For example, some oral appliances cause retraction of the upper dentition back and protraction of the lower dentition forward, leading to reduction of the overjet or causing edge to edge or under bite development because the upper teeth move behind the lower teeth. As a result, daytime breathing may become difficult for the patient without the appliance in the mouth, especially when they are involved with physical exertion that requires more air flow. This side effect of the conventional ODs most often requires periodic activation of the device to regain its efficiency during the bed-time use. Accordingly, there remains a need for oral devices that efficiently reduce the sleep apnea while minimizing the unwanted side effects.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Specific details of several embodiments of representative masticatory and airway stabilizing orthotic oral appliances and associated methods for use are described below. The oral appliances can be used for treating sleep-disordered breathing and related masticatory and temporomandibular disorders. A person skilled in the art will also understand that the technology may have additional embodiments, and that the technology may be practiced without several of the details of the embodiments described below with reference to FIGS. 1A-6C.

In some embodiments of the present technology, the oral appliance moves the patient's lower jaw forward during the sleep to create more space in the airway behind the tongue. In some embodiments, the oral appliance (hereinafter referred to as "appliance," "dental appliance," and/or "oral appliance") may be securely attached to the upper teeth, while lightly touching inner side of the lower teeth or gingival or soft tissue surrounding the lower teeth and by stimulating the advancing lower jaw muscles, guiding the lower jaw to more forward position without pushing or pulling the lower jaw. When the patient sleeps, lightly touching (i.e., stimulating) the lower teeth causes the patient to subconsciously respond by moving the lower jaw away from the dental appliance that touches the lower teeth. This subconscious response is sometimes called mechanoreceptor activation. As the lower jaw is moved forward, the airways behind the patient's palate, tongue and below the tongue open, thus reducing the air blockage that causes obstructive sleep apnea (OSA).

In some embodiments, the appliance may include openings for air to ease patient's breathing. In some embodiments, the appliance may include adjustable extenders (e.g., jack screws) that can adjust position of the lower section of the appliance (e.g., the section that touches the teeth) with respect to the upper section of the appliance (e.g., the section that attaches to the upper teeth of the patient). In some embodiments, the appliance may be made as a combination of plastic (e.g., acrylic) and one or more stiffening members (e.g., relatively strong wires encapsulated in the plastic).

Figure 1A:
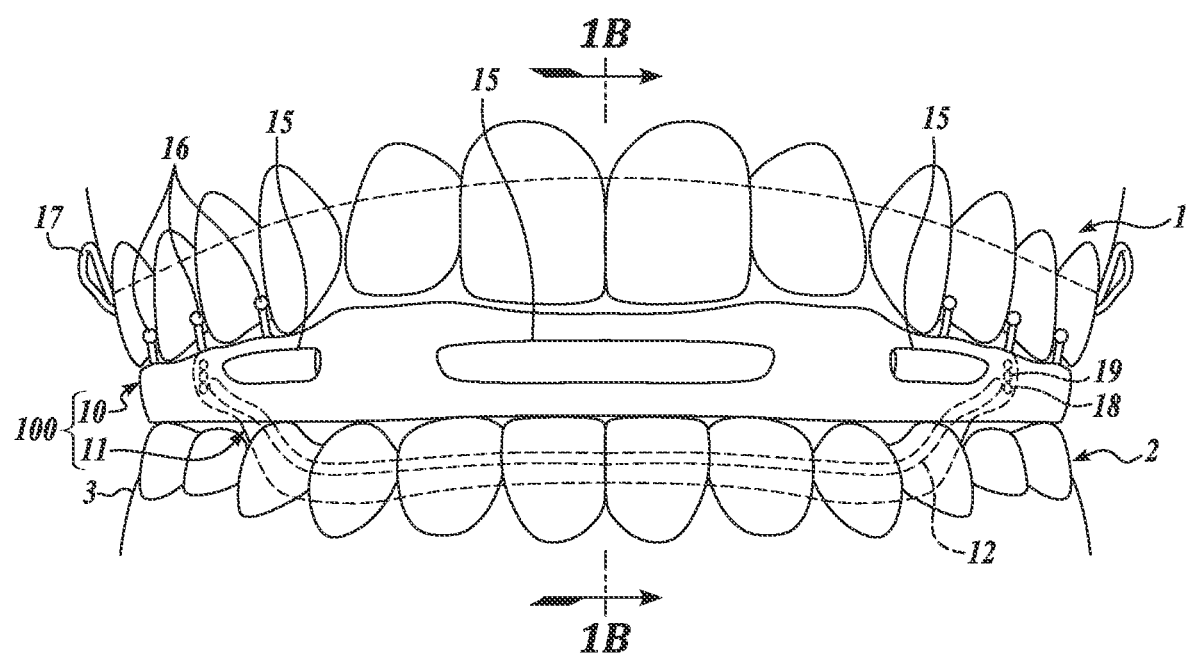
FIG. 1A is a front view of an oral appliance in accordance with an embodiment of the present technology.

FIGS. 1A-1D show several views of an oral appliance 100 in accordance with an embodiment of the present technology. FIG. 1A is a front view of the oral appliance 100 in accordance with an embodiment of the present technology. The illustrated oral appliance 100 includes an upper section 10 and a lower section 11. The upper section 10 is generally positioned between upper teeth 1 and lower teeth 2, and behind the upper teeth 1. In some embodiments, the upper section 10 can be attached to the upper teeth 1 with ball hooks 16, and/or Adam clasps 17. The illustrated upper section 10 includes air openings 15 to ease patient's breathing (e.g., if the patient needs to breathe through the mouth instead of through the nose because of, for example, allergies). The lower section 11 is generally behind the lower teeth 2 and gums 3. The lower section 11 can be repositioned with respect to upper section 10 using extenders 19 and/or sliders 18, as explained in more detail with respect to FIG. 1B below.

Figure 1B:
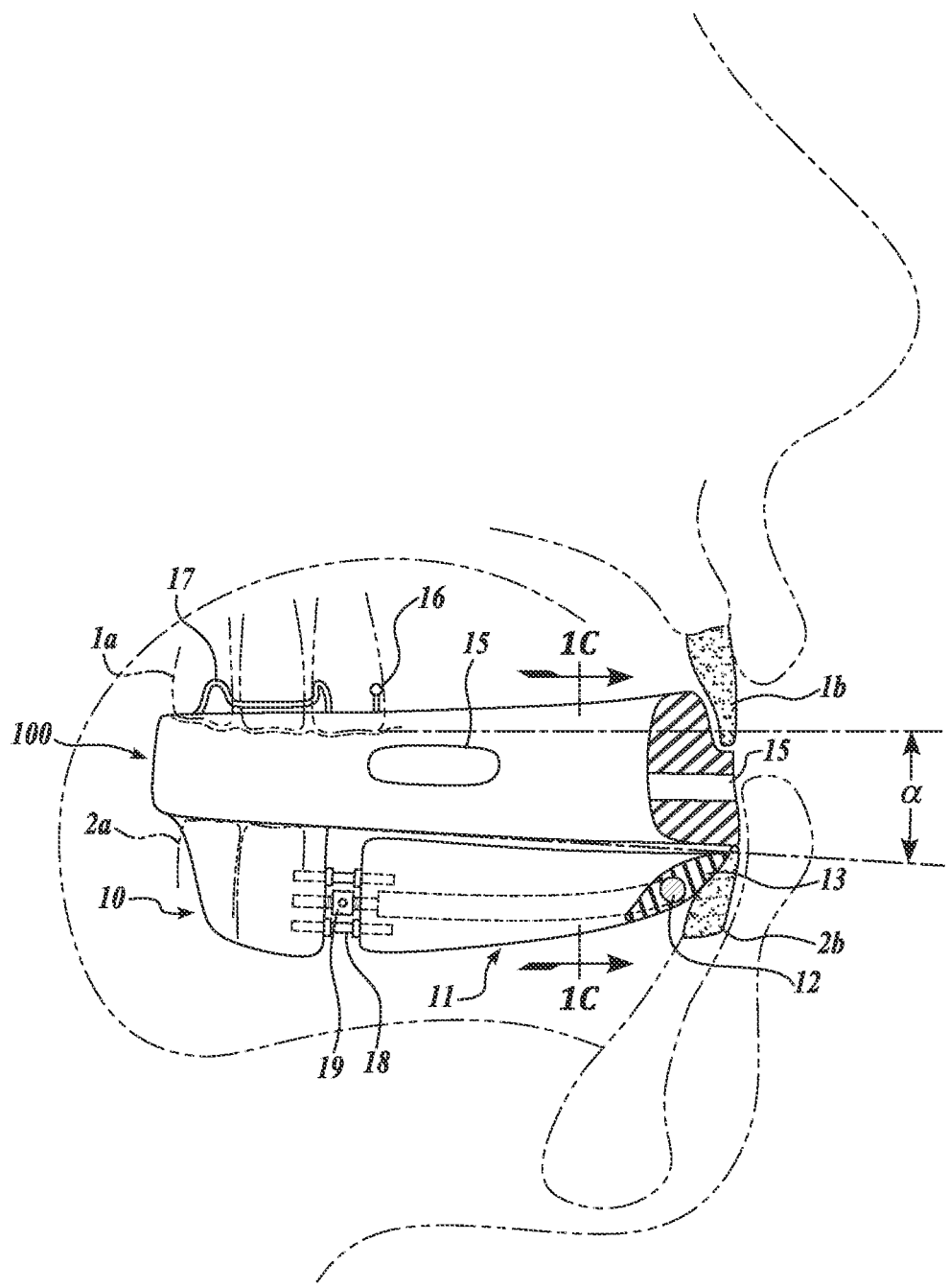
FIG. 1B is a cross-sectional side view of an oral appliance in accordance with an embodiment of the present technology.

FIG. 1B is a cross-sectional side view 1B-1B of the oral appliance 100 in accordance with an embodiment of the present technology. In some embodiments, the upper section 10 can be shaped to keep patient's jaw slightly opened by spreading patient's molar teeth. For example, the upper section 10 can space apart upper molar teeth 1a and lower molar teeth 2a to form an angle α between the chewing surfaces of the upper molar teeth 1a and the lower molar teeth 2a. In some embodiments, the angle α can range from about 0° to about 30°, or more if required. This facilitates the opening of the lower jaw when the lower jaw is moved forward to increase the lower facial height and vertical space for the tongue, and helps to move tongue forward out of the airway.

In some embodiments, the upper section 10 is attached to the upper teeth 1 (e.g., the molars 1a), and is supported by the ball hooks 16, Adam clasps 17 and/or other attachments. The upper section 10 can be secured in place by one or more molars on each side of the upper jaw, and the molars 2a in the lower jaw, and between the front teeth 1a/1b at the front of the mouth. The lower section 11 can be connected to the upper section 10 with an extender 19 (e.g., a jackscrew) and one or more sliders 18. The activation of the extenders 19 on the sides of the oral appliance 100 advances the lower section of the appliance forward. The activation may be performed by, for example, a skilled dental professional or a patient. In some embodiments, the sliders 18 may reduce the incidence of the appliance binding caused by an uneven advancement of the extenders 19 at the two sides of the appliance. The sliders 18 may be, for example, a combination of a pin and a sleeve. As the lower section 11 touches the inner side of the lower teeth 2 or their surrounding soft tissue, this contact (i.e., a tactile stimulation) of the lower teeth causes the patient to subconsciously respond by moving the lower jaw away from the dental appliance (i.e., mechanoreceptor activation). As explained above, when the lower jaw is moved forward, the airways open behind the patient's palate, and behind and below the tongue, thus reducing the air blockage that causes obstructive sleep apnea. Therefore, in some embodiments, the extender 19 may be adjusted forward before the patient falls asleep.

For the growing patients, a forward posturing of the lower jaw can accelerate the overall sagittal growth of the lower jaw, therefore improving the class two facial skeletal discrepancies caused by small lower jaw, and helping to treat the sleep apnea. In at least some embodiments, a treatment can combine intra temporomandibular joint injection of Platelet Rich Plasma with the oral appliance 100, and may enhance the rate of jaw growth, which, in turn further reduces the air blockage that causes the obstructive sleep apnea.

The oral appliance 100 can be made of a polymer, e.g., a clear or colored glow-in-the dark acrylic that makes the recovery of the appliance at bed time easier. In some embodiments, the polymer body of the oral appliance 100 may be strengthened by a stiffening member 12 (e.g., a wire). In some embodiments, the occlusal thickness of the acrylic (i.e., thickness of the appliance between the upper and lower teeth) can be 5-7 mm. In some embodiments, the occlusal thickness of the acrylic can be selected to create vertical opening of 7-8 mm between lower and upper front teeth.

Figure 1C:
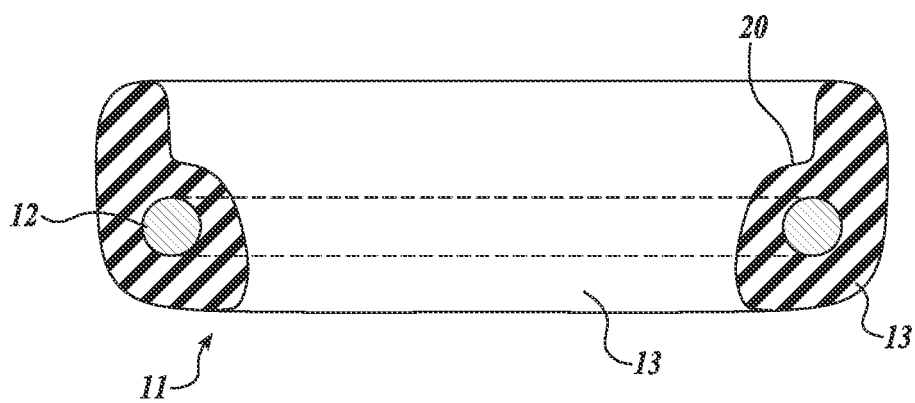
FIG. 1C is a cross-sectional side view of an oral appliance in accordance with an embodiment of the present technology.

FIG. 1C is a cross-sectional side view 1C-1C of the oral appliance 100 in accordance with an embodiment of the present technology. In some embodiments, the lower section 11 includes a lining 13 that is reinforced by the stiffening member 12. In some embodiments, the lining 13 may be shaped to form a tongue resting plateau 20 that provides a supporting surface for the patient's tongue to hold it up and forward from the floor of the mouth. Generally, the additional space for the patient's tongue easies the breathing and reduces the severity of sleep apnea.

Figure 1D:
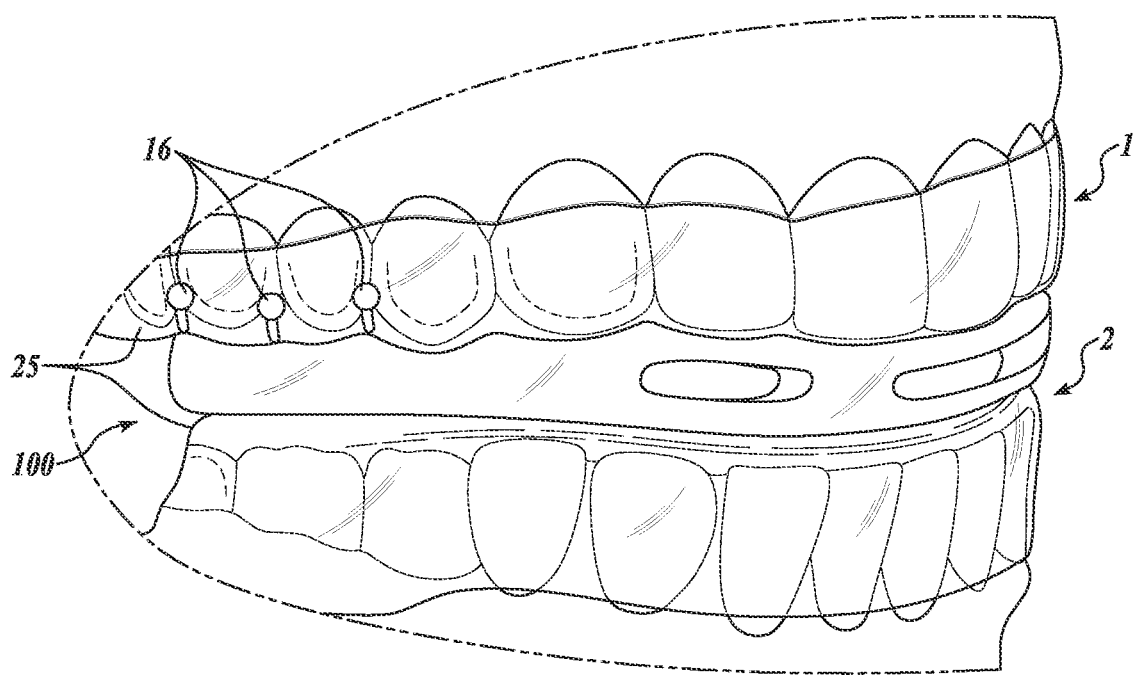
FIG. 1D is a partially schematic side view of an oral appliance in accordance with an embodiment of the present technology.

FIG. 1D is a partially schematic side view of an oral appliance in accordance with an embodiment of the present technology. The illustrated embodiment of the oral appliance may be used in conjunction with a teeth liner 25 (e.g., a clear aligner, an Essix retainer, etc.) The teeth liner 25 can be used to straighten the patient's upper and/or lower teeth while using the oral appliance to treat the sleep apnea or masticatory and temporomandibular disorders. In some embodiments, the oral appliance 100 may be attached to the teeth liner using, e.g., the ball hooks 16, other means of attachment or permanently cemented by adhesive. In some embodiments, the ball hooks 16 may be attached directly to the patient's teeth. The upper section 10 of the oral appliance 100 may be fitted over the occlusal surface of the teeth liner 25. Generally, the teeth liner 25 improves retention of the upper and/or lower teeth, and prevents any unwanted movement of the teeth. The teeth liner 25 allows gradual tooth movement to progress through orthodontic treatment to improve the bite, masticatory and temporomandibular disorders, and to manage or treat the sleep apnea. The teeth liner 25 for upper and/or lower teeth may also be used in conjunction with the other embodiments of the oral appliance described below.

Figure 2A:
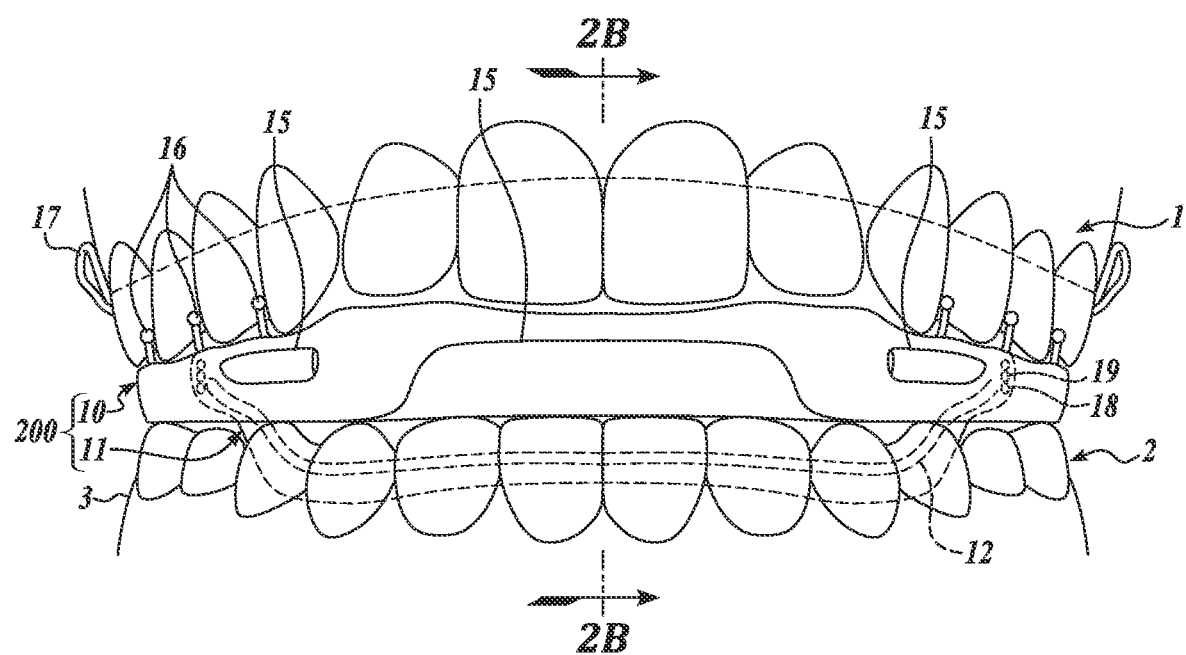
FIG. 2A is a front view of an oral appliance in accordance with an embodiment of the present technology.
Figure 2B:
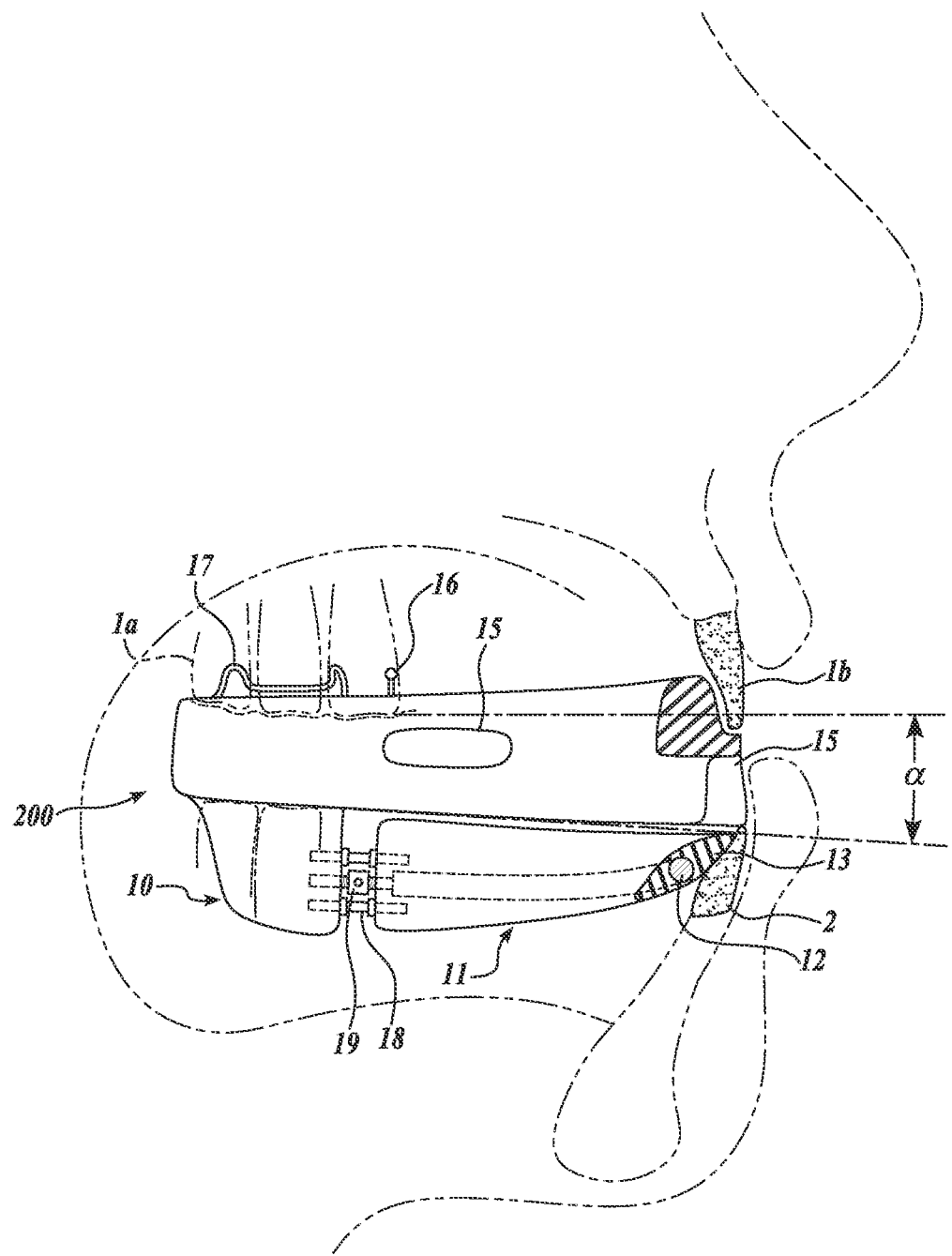
FIG. 2B is a cross-sectional side view of an oral appliance in accordance with an embodiment of the present technology.
Figure 2C:
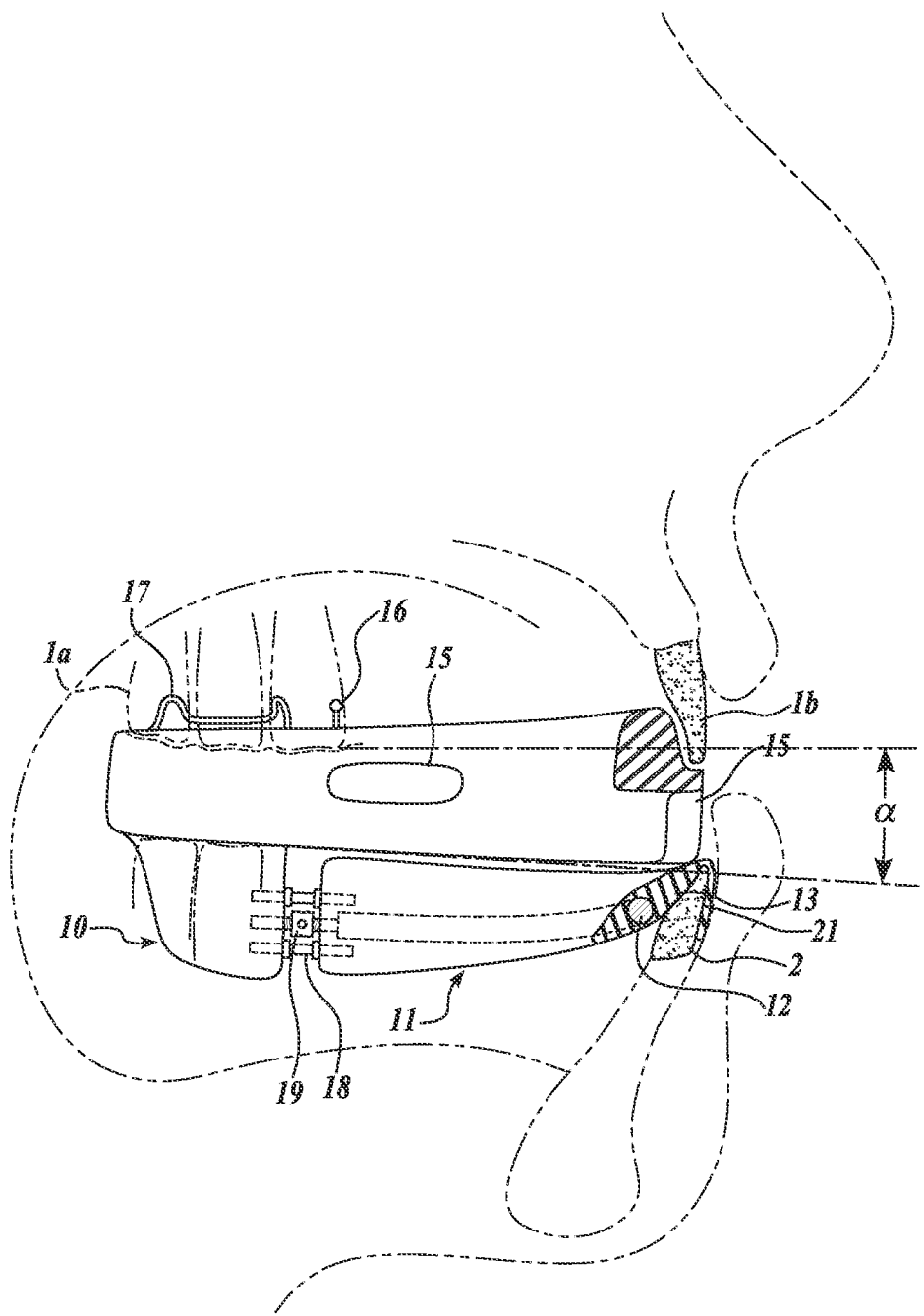
FIG. 2C is a cross-sectional side view of an oral appliance in accordance with another embodiment of the present technology.

FIGS. 2A-2C show several views of an oral appliance 200 in accordance with an embodiment of the present technology. FIG. 2A is a front view of the oral appliance 200 in accordance with an embodiment of the present technology. The oral appliance 200 includes several elements that are generally similar to those of the oral appliance 100.

In some embodiments, one or more air openings 15 can be enlarged by removing portions of the upper section 10. For example, the air opening 15 in the middle of the upper section 10 may be extended up to the lower edge of the upper section 10 or up to the upper edge of the upper section 10. In some embodiments, the side air openings 15 may be enlarged, while the air opening 15 in the middle remains smaller than the side air openings 15.

FIG. 2B is a cross-sectional side view 2B-2B of the oral appliance 200 in accordance with an embodiment of the present technology. The opening 15 in the upper section 10 extends through the lower edge of the upper section 10. The larger opening 15 makes the patient's breathing easier, therefore further reducing the incidence of sleep apnea. The larger opening 15 may also facilitate wearing an auxiliary tongue holding appliance (not shown) between the front teeth for the patients with large tongues or those who need to sleep on the back. The auxiliary tongue holding appliance may counteract the gravity to prevent or at least reduce the incidence of the tongue falling in the airway.

FIG. 2C is a cross-sectional side view 2B-2B of the oral appliance 200 in accordance with another embodiment of the present technology. The illustrated embodiment includes a teeth cover 21 that covers the lower teeth 2. In some embodiments, the teeth cover 21 may be made of the same material as the lining 13 of the lower section 11, e.g., the teeth cover 21 can be made of acrylic. In at least some embodiments, the retention of the lower teeth is improved by covering the lower teeth 2 with the teeth cover 21.

Figure 3A:
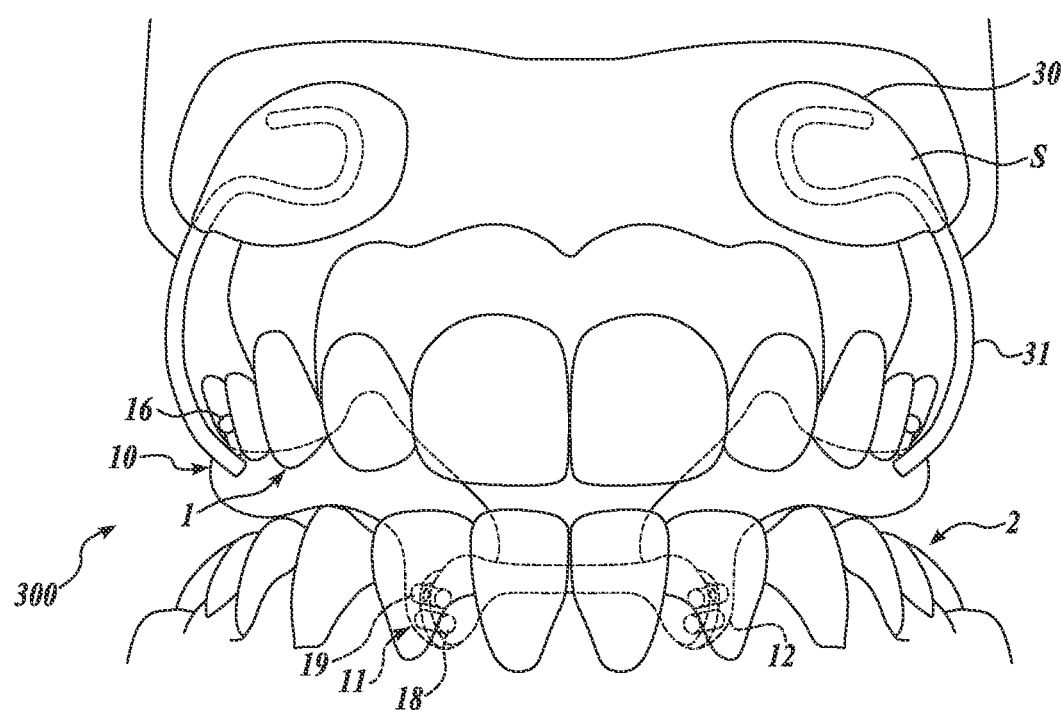
FIG. 3A is a front view of an oral appliance in accordance with an embodiment of the present technology.
Figure 3B:
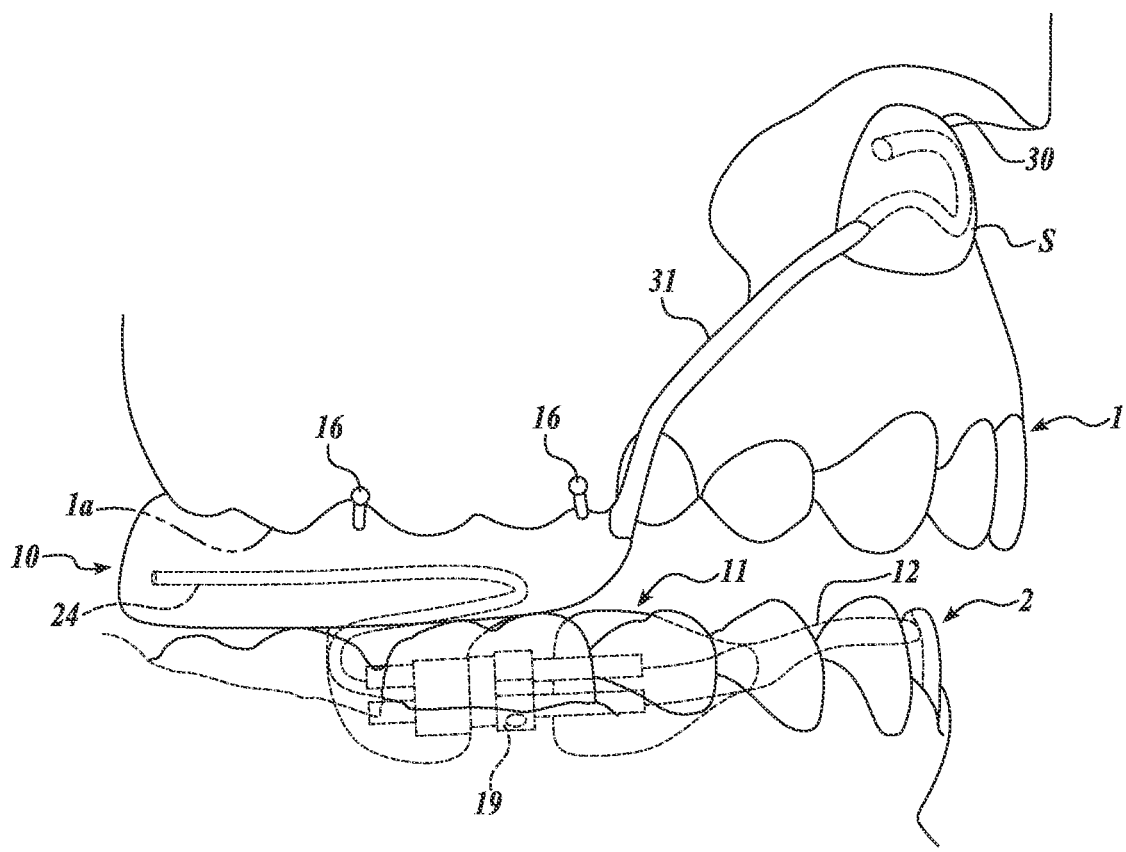
FIG. 3B is a partially schematic side view of an oral appliance in accordance with an embodiment of the present technology.
Figure 3C:
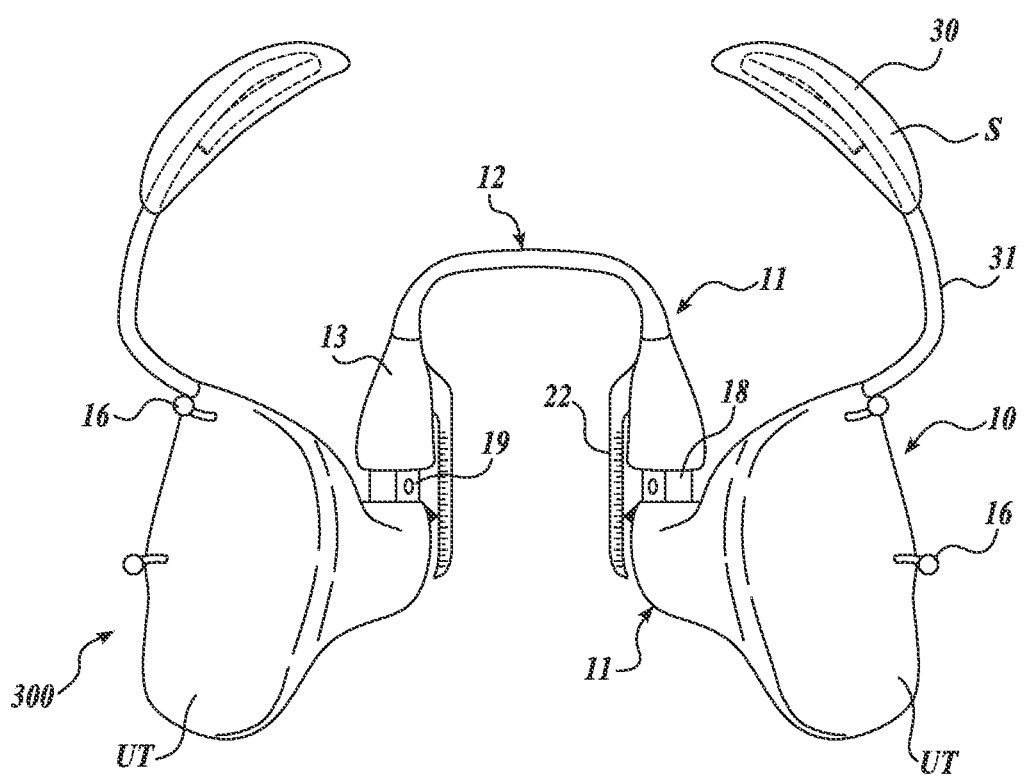
FIG. 3C is a top view of an oral appliance in accordance with an embodiment of the present technology.
Figure 3D:
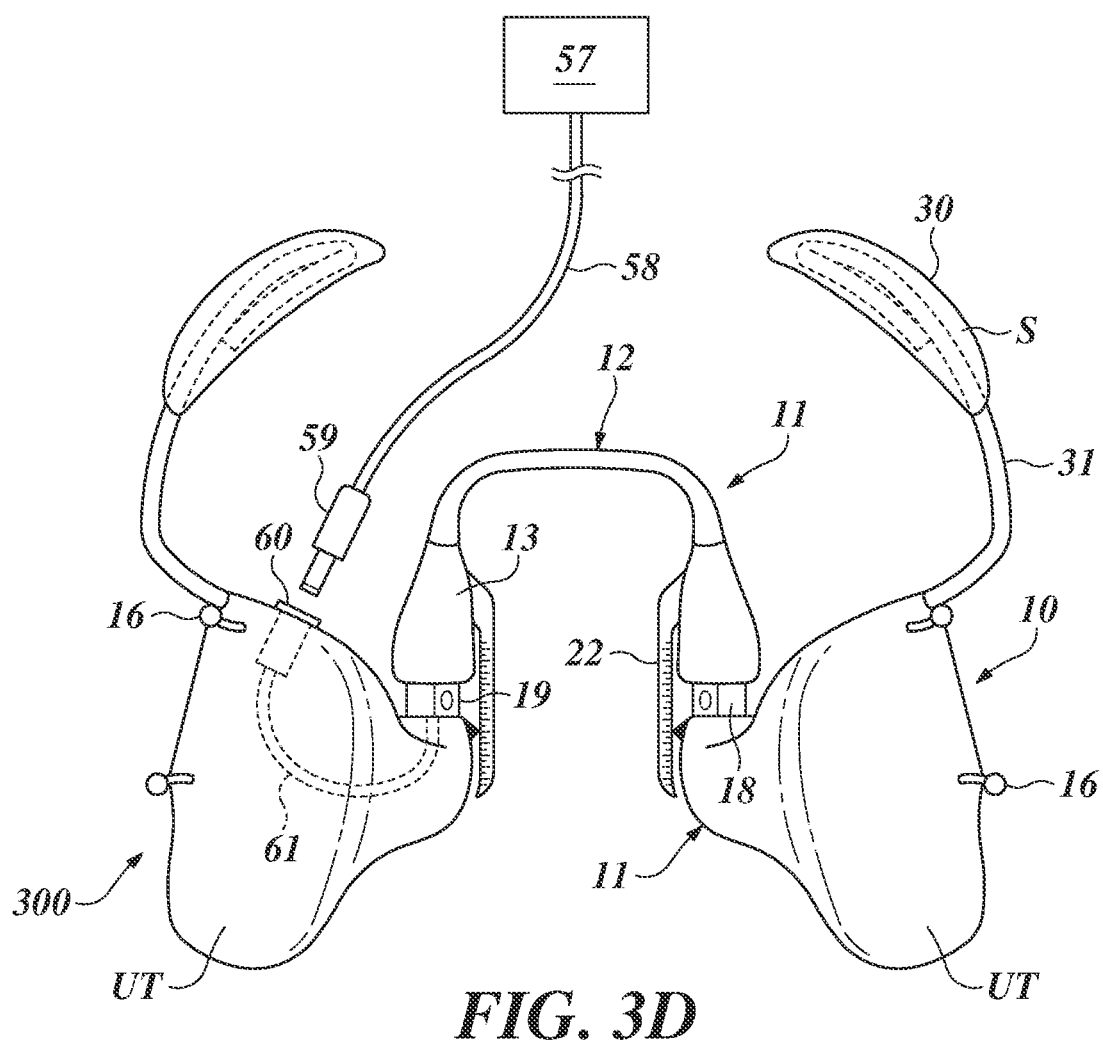
FIG. 3D is a top view of an oral appliance in accordance with an alternative embodiment of the present technology, using electricity.

FIGS. 3A-3C show several views of an oral appliance 300 in accordance with an embodiment of the present technology. FIG. 3A is a front view of the oral appliance 300 in accordance with an embodiment of the present technology. In the illustrated embodiment, the front part of the upper section 10 is removed to create a smaller appliance, to increase opening for breathing (e.g., if the patient cannot breath through the nose because of allergy or cold), and/or to increase space for the tongue. The oral appliance 300 includes side flaps 30 that can spread the upper lip attached to the nasal nares, therefore opening the nasal passages of the patient to improve breathing. In some embodiments, surfaces S of the side flaps 30 are positioned between the upper lip and the upper gums of the patient. Flap attachments 31 connect the side flaps 30 to the upper section 10, and can provide structural integrity to the surfaces S. The flap attachments 31 can bias the side flaps 30 toward the front and/or side of the patient's face to spread the upper lip attached to nasal nares to facilitate spreading apart of the nasal passages. The flap attachments 31 are described with reference to the oral appliance 300, but the flap attachments 31 may be used in conjunction with other embodiments of the oral appliances.

FIG. 3B is a partially schematic side view of the oral appliance 300 in accordance with an embodiment of the present technology. The extender 19 (e.g., a jackscrew) connects the upper section 10 to the lower section 11. Adjusting the extenders 19 on both sides of the oral appliance moves the lower section 11 forward and into contact with the lower teeth 2. In some embodiments, the upper section 10 may include a reinforcement wire 24 (e.g., a steel wire) for improved structural integrity of the upper section 11.

FIG. 3C is a top view of an oral appliance in accordance with an embodiment of the present technology. In the illustrated view, the upper teeth (not shown) press against surfaces UT of the upper section 10. The sliders 18 and the extenders 19 can advance the lower section 11 forward into contact with the lower teeth. The movement of the lower section 11 may be observed and measured with one or more adjustment indicators 22 (e.g., a graded scale). In some embodiments, the indicator 22 has a smooth surface area that can shield the tongue against touching the extender 19 for improved comfort. In some embodiments, the stiffening member 12 may be at least partially exposed out of the lining 13. In some embodiments, the exposed stiffening member 12 may be connected to an electric stimulator 57 (e.g., a source of low-voltage pulses). In one embodiment, electric stimulator is positioned outside of the patients mouth and connected by an insulated wire 58, which terminates a jack 59 that plugs into a socket 60, with a further wire connected to stiffening member 12 and metal indicator 22. When the stiffening member 12 touches the tongue, the electrical pulses can activate the tongue muscles and can cause forward projection and holding of the tongue to prevent or at least reduce the incidence of the tongue falling backward, especially when the patient is sleeping on the back. In some embodiments, the exposed stiffening member 12 and the electric stimulator can be connected to a sleep testing device. Depending on the severity of the patient's apnea/hypopnea index, the sleep testing device may increase the amplitude of the electrical impulses to activate the tongue for a more effective opening of the airway. In other embodiments, the stiffening member 12 may be completely encapsulated within the lining 13.

Figure 4A:
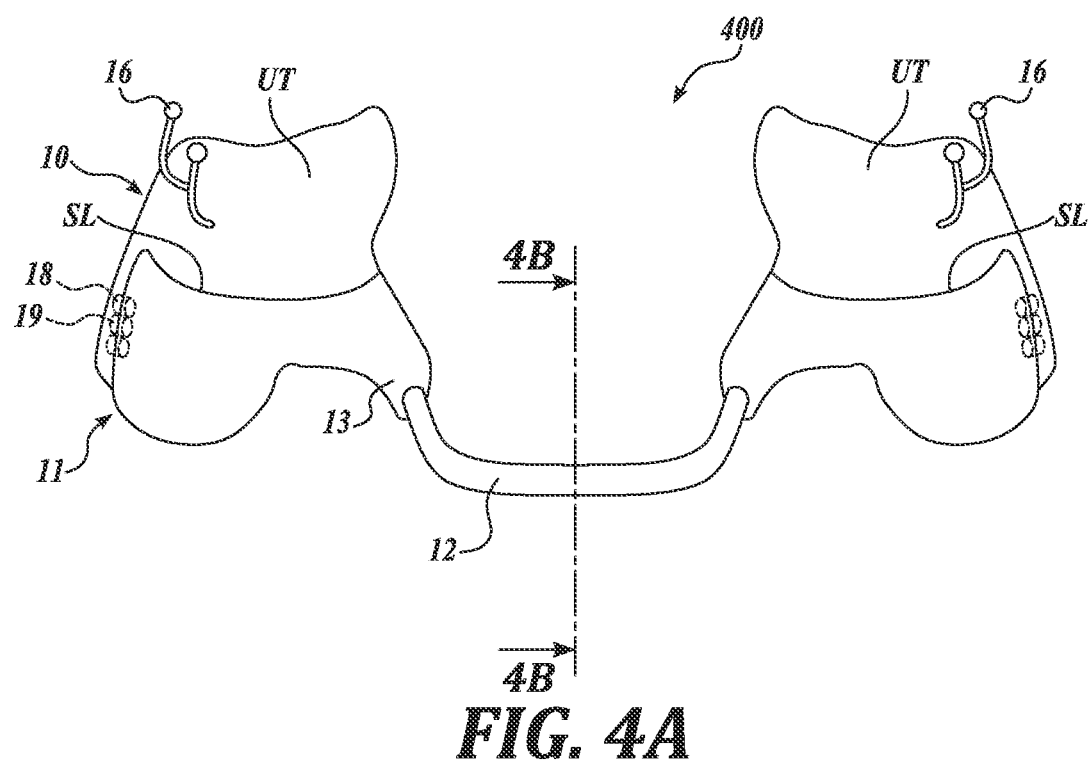
FIG. 4A is a front view of an oral appliance in accordance with an embodiment of the present technology.

FIGS. 4A-4D show several views of an oral appliance 400 in accordance with an embodiment of the present technology. FIG. 4A is a front view of the oral appliance 400 in accordance with an embodiment of the present technology. For clarity of the drawings, patient's teeth are not shown. With the illustrated embodiment, patient's upper teeth would press against the surfaces UT, and the stiffening member 12 (or the lining 13) would guide the lower jaw forward.

Figure 4B:
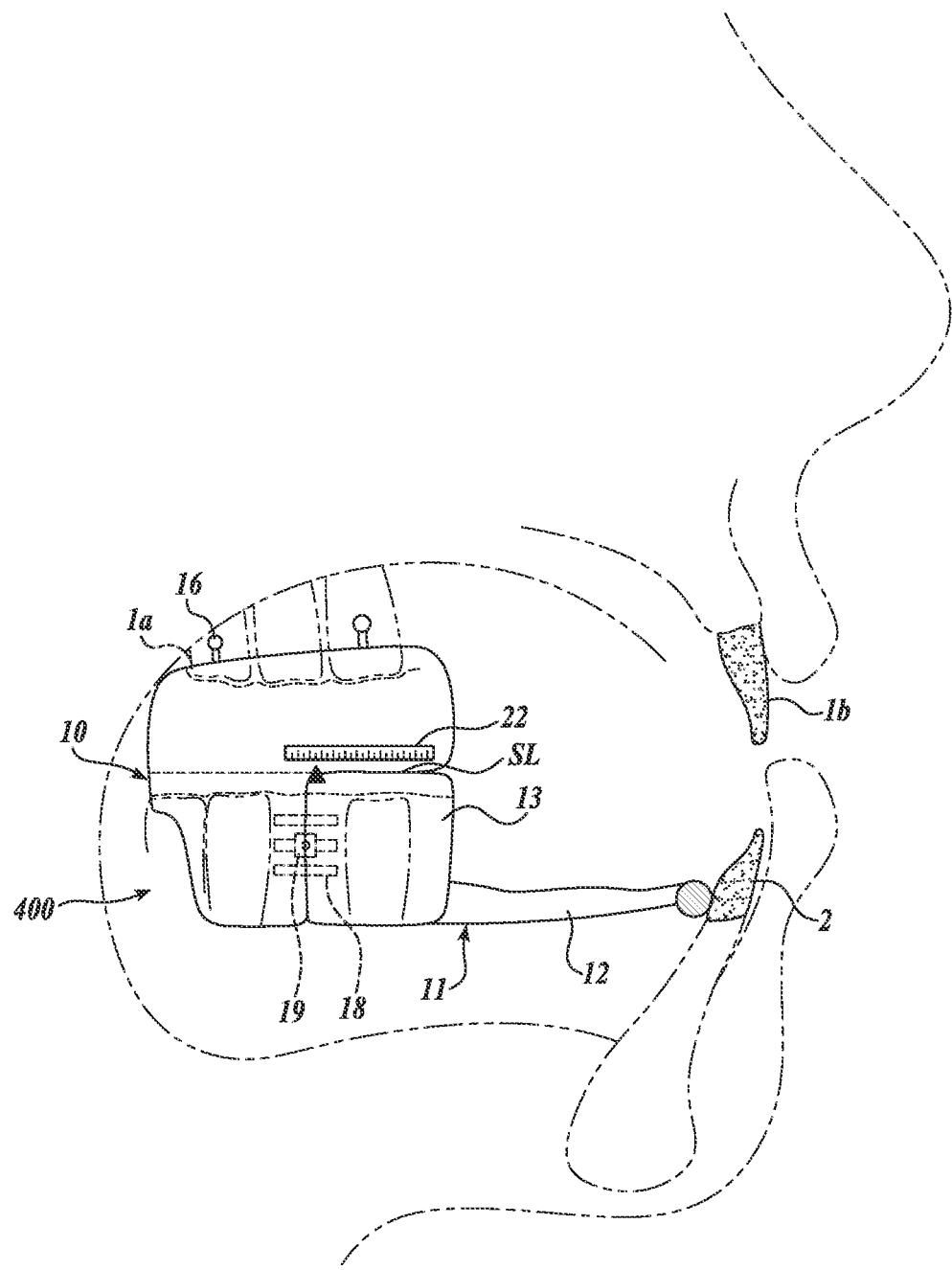
FIG. 4B is a cross-sectional side view of an oral appliance in a retracted position in accordance with an embodiment of the present technology.
Figure 4C:
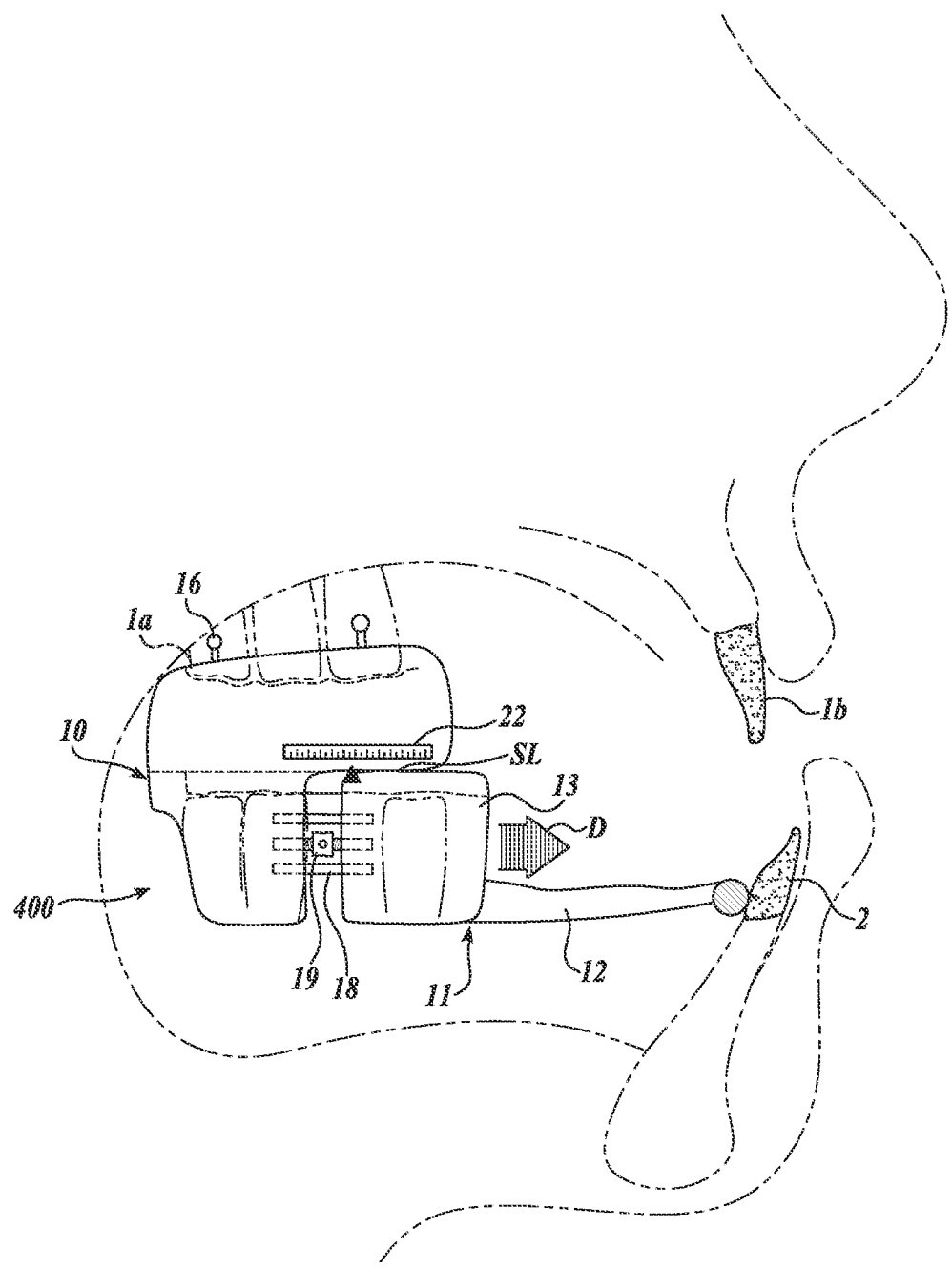
FIG. 4C is a cross-sectional side view of an oral appliance in an extended position in accordance with an embodiment of the present technology.

FIGS. 4B and 4C are cross-sectional side views 4B-4B of the oral appliance 400 in accordance with an embodiment of the present technology. FIGS. 4B and 4C show the oral appliance 400 in its retracted and extended positions, respectively. In some embodiments, when in its retracted position, the oral appliance 400 may just slightly touch the lower teeth 2 of the patient, or may not touch the teeth at all. When extended in a direction D using the extenders 19, the lower section 11 gently touches the lower teeth or their surrounding soft tissue, therefore generating the mechanoreceptor impulses to guide the lower jaw posture forward. As the lower jaw moves forward, the patient's airways open, and the incidence of sleep apnea is generally reduced. In some embodiments, the lower section 11 can slide over a sliding surface SL of the upper section 10 when moving into the extended position and back. The sliding surface SL may provide additional stability and/or structural integrity to the oral appliance 400. The movement of the lower section 11 against upper section 10 may be observed and measured with one or more adjustment indicators 22 (e.g., a graded scale).

Figure 4D:
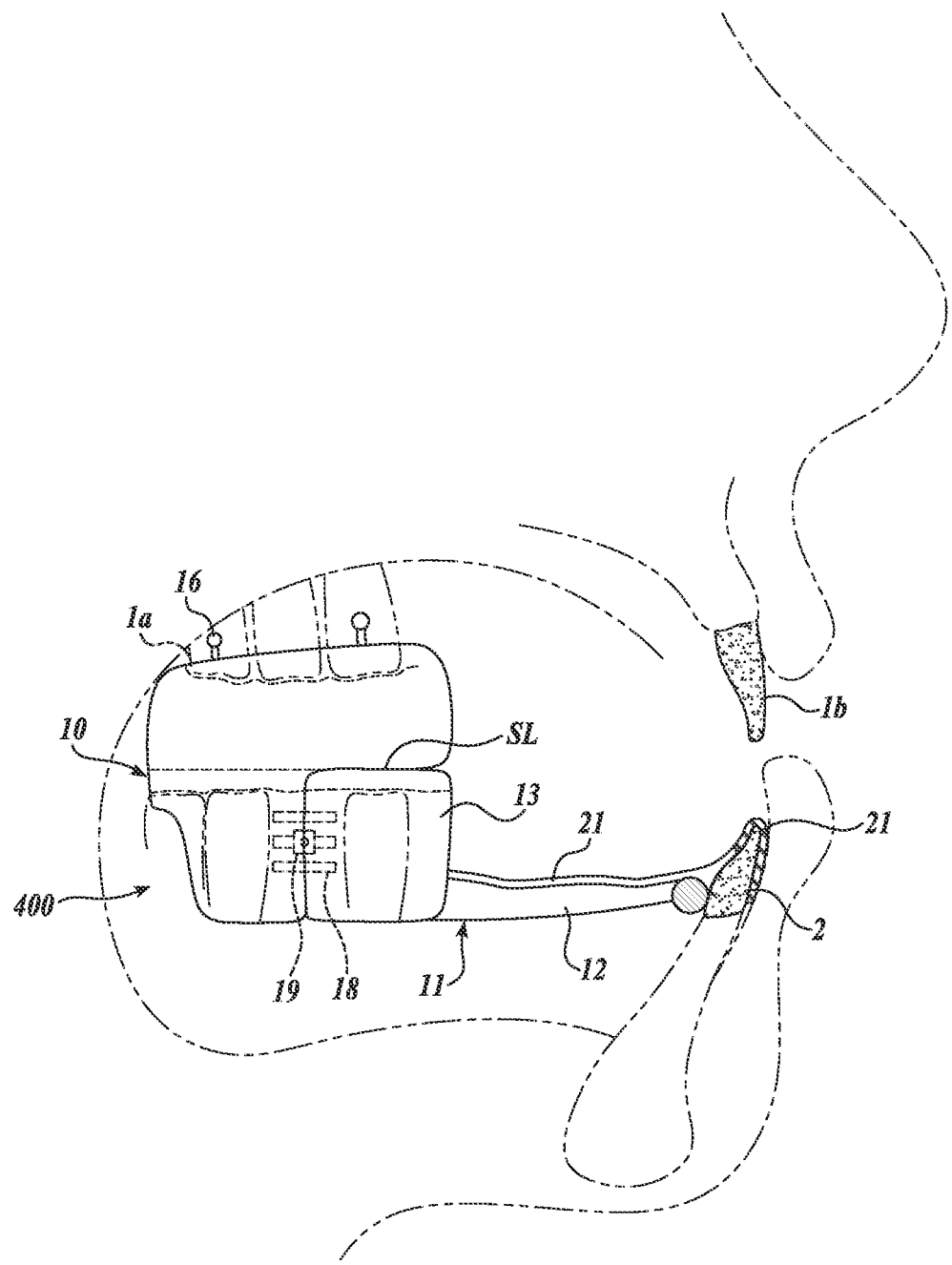
FIG. 4D is a cross-sectional side view of an oral appliance in accordance with an embodiment of the present technology.

FIG. 4D is a cross-sectional side view 4B-4B of the oral appliance 400 in accordance with an embodiment of the present technology. The oral appliance 400 is illustrated in its retracted position. The oral appliance 400 includes a lining 21 over the front teeth 2. In some embodiments, the lining 21 may reduce proclination and crowding of the lower teeth. In some embodiments, the lining 21 can replace the teeth liner 25.

Figure 5A:
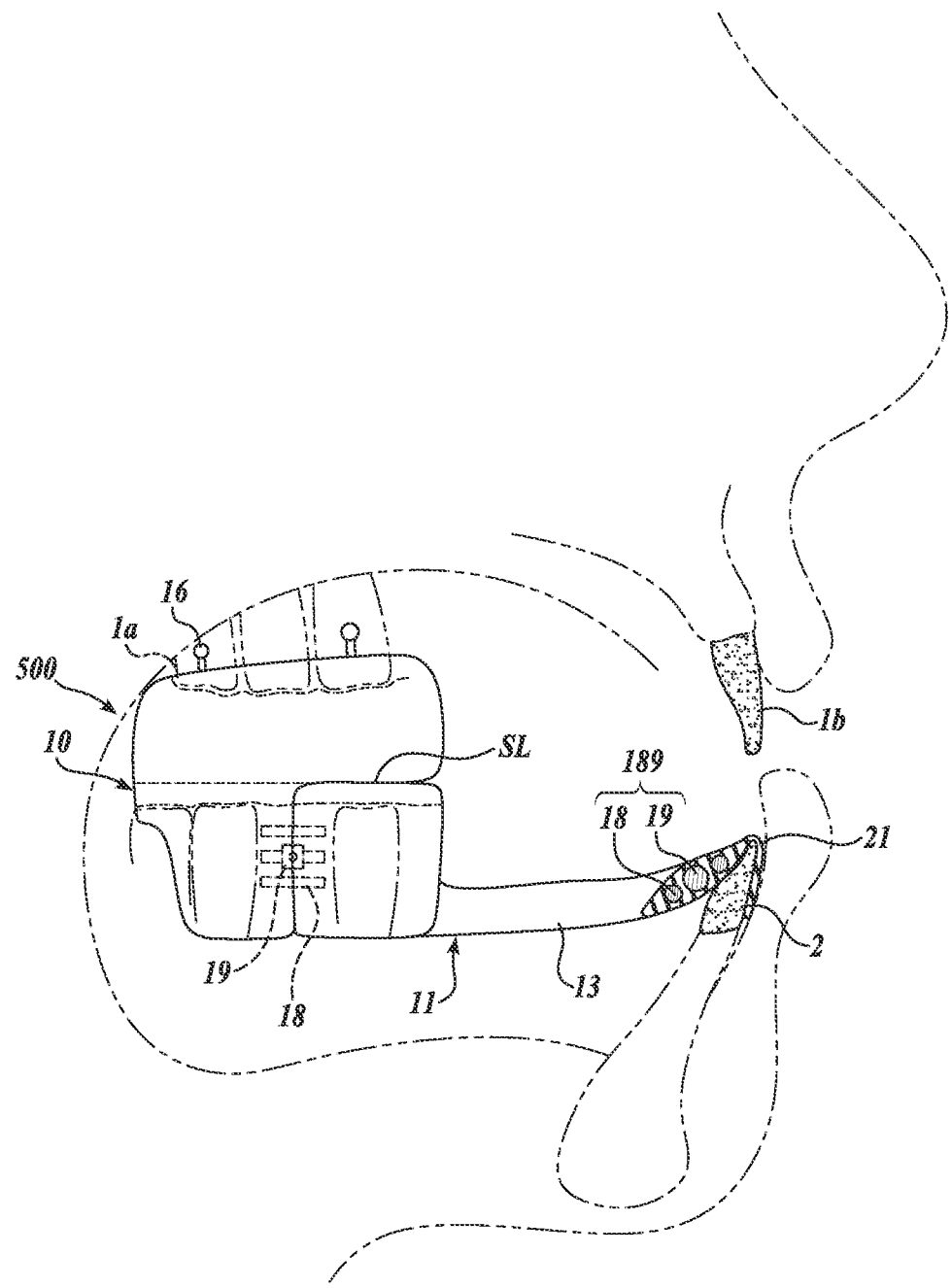
FIG. 5A is a cross-sectional side view of an oral appliance in accordance with an embodiment of the present technology.
Figure 5B:
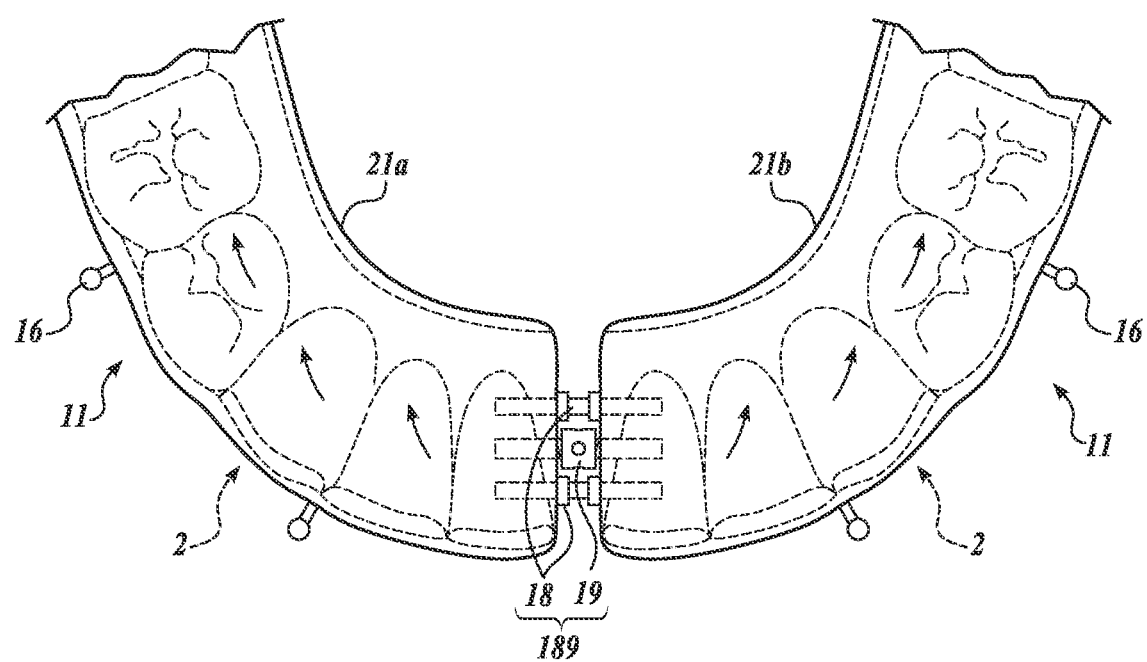
FIG. 5B is a top view of the lower section of an oral appliance shown in FIG. 5A.

FIGS. 5A and 5B show an oral appliance 500 in accordance with an embodiment of the present technology. FIG. 5A is a cross-sectional side view of the oral appliance 500 in accordance with an embodiment of the present technology. In some embodiments, the lower section 11 can slide against the upper section 10 along the surface SL. The lower section 11 may include a teeth spreading mechanism 189 having lateral sliders 18 and extender 19 in the lining 13. In some embodiments, the teeth spreading mechanism 189 may be proximate to the front lower teeth 2. The operation of the teeth spreading mechanism 189 is explained below in conjunction with FIG. 5B.

FIG. 5B is a top view of the lower section 11 of the oral appliance 500. In at least some embodiments, the teeth cover 21 includes two teeth cover sections 21a, 21b. The teeth cover sections 21a, 21b can be joined by the extender 19 and sliders 18 of the teeth spreading mechanism 189. The teeth cover sections 21a, 21b may be attached with the ball hooks 16 to the lower teeth 2 of the patient. In some embodiments, the teeth spreading mechanism 189 may include multiple extenders 19. In some embodiments, the teeth spreading mechanism 189 includes the extender 19, but does not include sliders 18. Activating the extender 19 causes the teeth cover sections 21a, 21b to move apart, therefore gradually spreading the teeth and jaw bones apart, too. In some instances, enlarging the lower dental arch and jaw also enlarges space for the air passages of the patient by creating more space for the tongue.

Figure 6A:
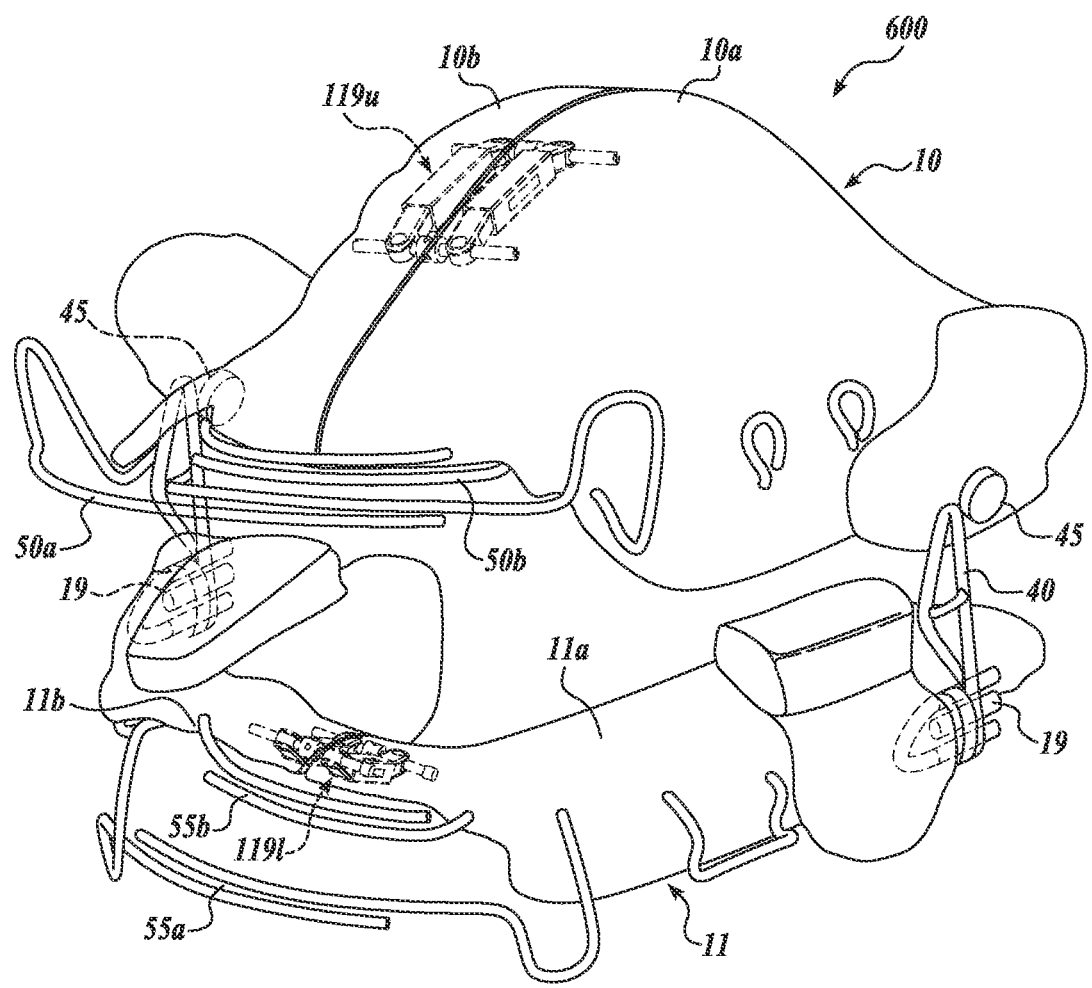
FIG. 6A is a side isometric view of an oral appliance in accordance with an embodiment of the present technology.
Figure 6B:
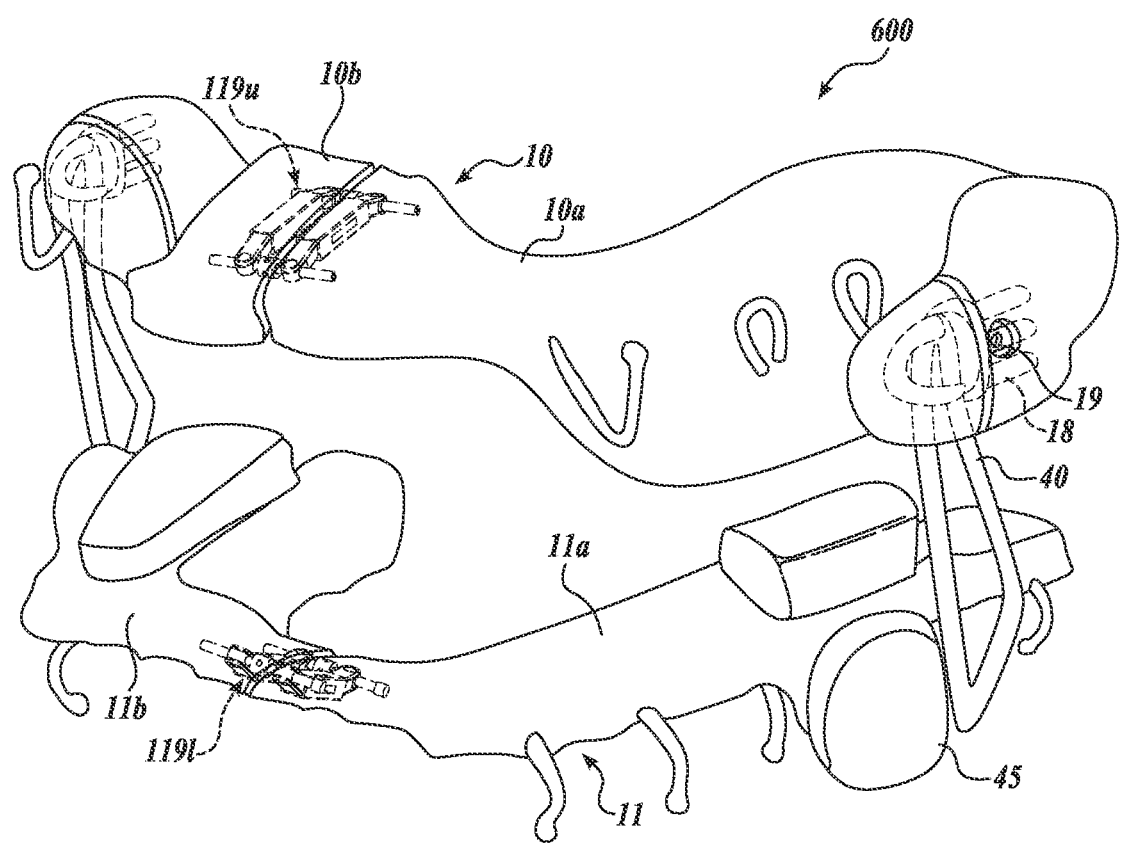
FIG. 6B is a side isometric view of an oral appliance in accordance with an embodiment of the present technology.
Figure 6C:
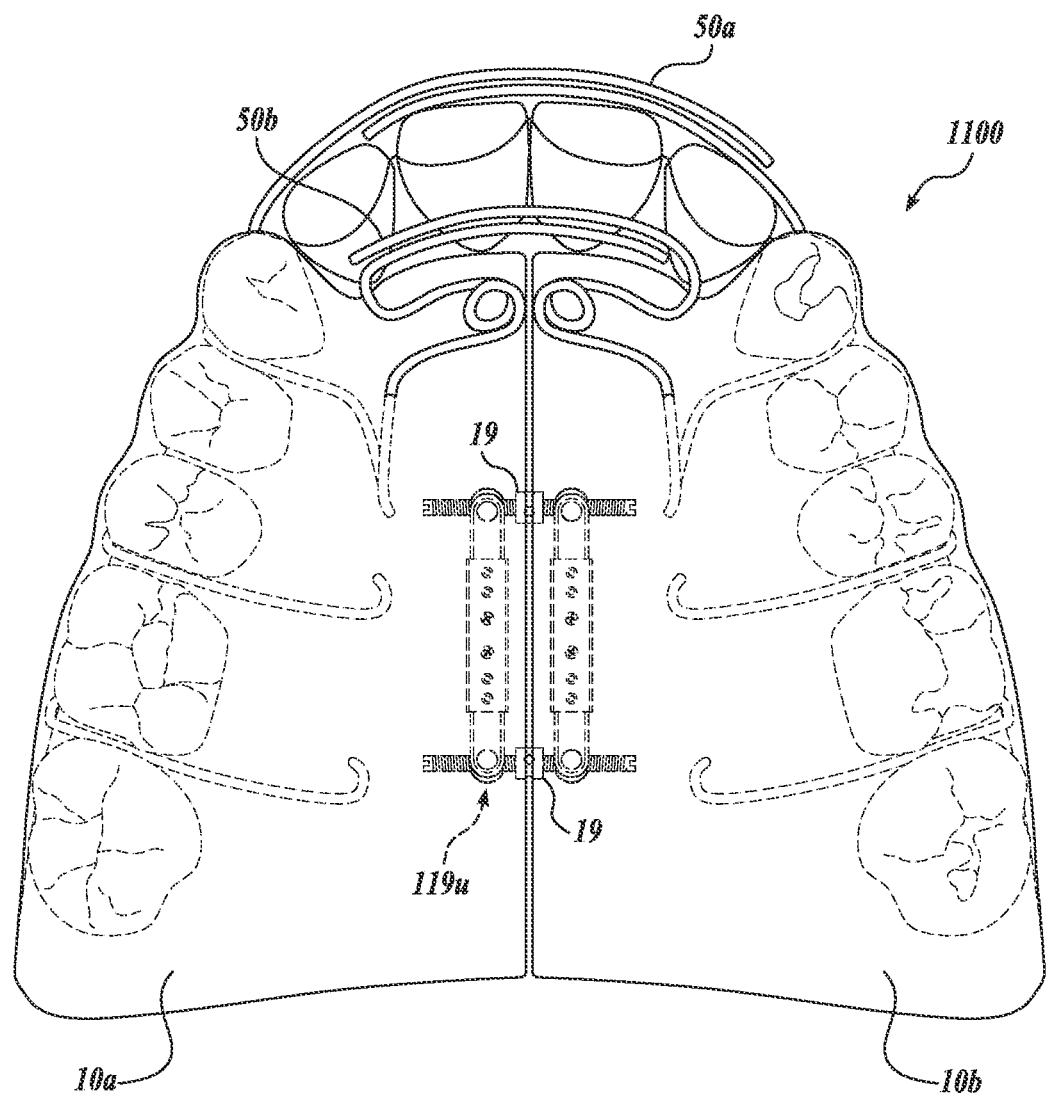
FIG. 6C is a top plan view of an oral appliance in accordance with an embodiment of the present technology.

FIGS. 6A-6C show several views of an oral appliance 600 in accordance with an embodiment of the present technology. FIG. 6A is a side isometric view of the oral appliance 600 in accordance with an embodiment of the present technology. The upper section 10 includes a right upper section 10a and a left upper section 10b connected with an upper separation mechanism 119u. In some embodiments, the upper section 10 may lie against the interior of the upper jaw. Activation of the upper separation mechanism 119u spreads apart the right/left upper sections 10a/10b. In turn, the teeth and bones of the upper jaw are also gradually pulled apart. In some instances, this separation of the teeth and bones of the upper jaw can enlarge space for the air passages of the patient by enlarging the nasal cavity and also by enlarging the palate creating more room for the tongue, so the tongue can move forward out of the airway. Analogously, activation of a lower separation mechanism 119l may separate right/left lower sections 11a/11b, which gradually pull apart the teeth and bones of the lower jaw to enlarge space for the air passages by creating more space for the tongue. In some embodiments, the extenders 19 provide the forward movement of the lower section 11 by pushing a post 40 against a protrusion 45.

In some embodiments, the upper section 10 and/or the lower section 11 may include teeth straightening extension arms. For example, lower teeth straightening extension arms 55a/55b may improve straightening of the lower teeth, and upper teeth straightening extension arms 50a/50b may improve straightening of the upper teeth.

FIG. 6B is a side isometric view of the oral appliance 600 in accordance with an embodiment of the present technology. In some embodiments, the upper section 10 and the lower section 11 are relatively small (in comparison to the embodiment illustrated in FIG. 6A), therefore less intrusive and easier to carry in the mouth for at least some patients. With the illustrated embodiment, the post 40 is carried by the upper section 10, and the protrusion 45 is carried by the lower section 11.

FIG. 6C is a top plan view of an oral appliance in accordance with an embodiment of the present technology. FIG. 6C illustrates position of teeth with respect to the upper teeth straightening extension arms 50a/50b.

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

The embodiments of the invention in which an exclusive property or privilege is claimed are as follows:

1. A method of treating sleep disordered breathing in a human sleep apnea patient having a mouth having upper teeth and lower teeth, including upper molars, and a tongue, the method comprising:
   a. providing an oral appliance made of a polymer that is strengthened by a stiffening member; the appliance having:
      i. an upper section, adapted to be engaged to and suspended from an outer side of the upper molars and configured to provide separation between the upper teeth and lower teeth of the patient when said upper section is suspended from the upper molars;
      ii. a lower section, suspended from said upper section when said upper section is suspended from the outer side of the upper molars, said lower section including a lining that is reinforced by the stiffening member, wherein the stiffening member is at least partially exposed out of the lining and connected to an electric stimulator;
   b. before the sleep apnea patient goes to sleep, placing said appliance into the mouth of the patient, and engaging said upper section to the outer side of the upper molars,
thereby separating the upper and lower teeth; and
   c. permitting said lower section to touch against one of a group consisting of a lower section of lower front teeth and the gums supporting the lower front teeth, thereby stimulating a mechanoreceptor impulse and causing a lower jaw of the patient to be moved forward, creating more airway space, and wherein the electric stimulator provides a source of low-voltage pulses to activate tongue muscles when the tongue touches the stiffening member to cause forward projection and holding of the tongue to prevent the tongue from falling backwards and causing airway obstruction, thereby preventing sleep apnea.

2. The method of claim 1, wherein said upper section is configured to extend from a first side of the mouth across a front of the mouth, and to a second side of the mouth, opposed to the first side of the mouth.

3. The method of claim 2, wherein said upper section includes an air opening in a front section, configured to assist patient breathing.

4. The method of claim 1, further wherein an aligner is placed over the upper and lower teeth, before the patient goes to sleep and before placing said appliance in the mouth, and whereby said lower section touches against the lower front teeth, by touching against said aligner which is anchored over the lower teeth.

5. The method of claim 1, wherein said appliance further includes side flaps configured to project upwardly from the upper section to rest between an upper lip and front gums of the patient, when said upper section is suspended from the upper molars, thereby widening nasal passageways.

6. The method of claim 1, wherein said appliance includes a cover for the lower teeth and wherein said step of placing said appliance into the mouth includes fitting said cover for the lower teeth over the lower teeth.

7. The method of claim 1, wherein said upper section includes ball hooks and said ball hooks are used to suspend said upper section from the upper teeth of the patient.

8. The method of claim 1, wherein said upper section includes Adams clasps and said Adams clasps are used to suspend said upper section from the upper teeth of the patient.

9. The method of claim 1, wherein said lower section defines a tongue resting plateau.

10. The method of claim 1, further wherein the lower section provides a tongue resting plateau configured for lifting the tongue to ease breathing during sleep.

11. An oral appliance for treating sleep disordered breathing in a human patient having upper and lower teeth, including upper molars, and a tongue, the appliance made of a polymer that is strengthened by a stiffening member and comprising:
   a. an upper section, adapted to be engaged to and suspended from an outer side of the upper molars and configured to provide separation between the upper teeth and lower teeth of the patient when said upper section is suspended from the upper molars;
   b. a lower section suspended from said upper section when said upper section is suspended from the outer side of the upper molars, and positioned and shaped to contact one of a group consisting of a lower section of lower front teeth and gums supporting the lower front teeth, when advanced; said lower section including a lining that is reinforced by the stiffening member, wherein the stiffening member is at least partially exposed out of the lining and connected to an electric stimulator which is configured to provide a source of low-voltage pulses to activate tongue muscles when the tongue touches the stiffening member to cause forward projection and holding of the tongue to prevent the tongue from falling backwards and causing airway obstruction; and
   c. an extender configured to advance the lower section into contact with the lower teeth.

12. The oral appliance of claim 11, wherein said upper section is configured to extend from a first side of the mouth across a front of the mouth, and to a second side of the mouth, opposed to said first side of the mouth.

13. The oral appliance of claim 12, wherein said upper section includes an air opening in a front section, configured to assist patient breathing.

14. The oral appliance of claim 11, wherein said extender includes a helically threaded element.

15. The oral appliance of claim 11, further including side flaps configured to project upwardly from said upper section to rest between an upper lip and front gums of the patient, when said upper section is suspended from the upper molars and is configured for widening nasal passageways.

16. The oral appliance of claim 11, further including a cover for the lower teeth.

17. The oral appliance of claim 11, wherein said upper section includes ball hooks and said ball hooks are configured to suspend said upper section from the upper teeth of the patient.

18. The oral appliance of claim 11, wherein said upper section includes Adams clasps and said Adams clasps are configured to suspend said upper section from the upper teeth of the patient.

* * * * *